US007816550B2

(12) United States Patent
Thompson

(10) Patent No.: US 7,816,550 B2
(45) Date of Patent: Oct. 19, 2010

(54) PROCESSES FOR THE PRODUCTION OF ORGANOMETALLIC COMPOUNDS

(75) Inventor: David Michael Thompson, East Amherst, NY (US)

(73) Assignee: Praxair Technology, Inc., Danbury, CT (US)

( * ) Notice: Subject to any disclaimer, the term of this patent is extended or adjusted under 35 U.S.C. 154(b) by 1081 days.

(21) Appl. No.: 11/053,836

(22) Filed: Feb. 10, 2005

(65) Prior Publication Data
US 2006/0177577 A1 Aug. 10, 2006

(51) Int. Cl.
*C07F 15/00* (2006.01)

(52) U.S. Cl. .......................... 556/137; 556/35; 556/36; 556/138; 556/21; 987/9; 987/16; 987/18

(58) Field of Classification Search ................ 106/1.15
See application file for complete search history.

(56) References Cited

U.S. PATENT DOCUMENTS

| 6,262,198 | B1 | 7/2001 | Schlund et al. | |
|---|---|---|---|---|
| 6,403,735 | B1 | 6/2002 | Becke et al. | |
| 2004/0110632 | A1 | 6/2004 | Sita et al. | |
| 2004/0127732 | A1 | 7/2004 | Thompson et al. | 556/143 |
| 2006/0141155 | A1* | 6/2006 | Gordon et al. | 427/255.19 |

FOREIGN PATENT DOCUMENTS

WO   WO 2004052896 A1 *   6/2004

OTHER PUBLICATIONS

Bailey et al., Dalton 12, p. 1887-1891, May 2000.*
Clark et al., Polyhedron 20(15-16), p. 1875-1880, Jun. 2001.*
Casey C. McComas et al., "Neutral Ru($\eta^5$-pyrrole) Complexes, Synthesis and Structure of Diazaruthenocenes and Ru(1-3:5-6-($\eta$5-C8H11)(($\eta^5$-pyrrole) Complexes", *Organometallics* 2000, 19, 2853-2857.
M. Rawkowski DuBois "The activation of $\eta^5$-pyrrole complexes toward nucleophilic attack", *Coordination Chemistry Reviews 1998*, 174, 191-205.
M. Rawkowski DuBois et al "Nucleophilic Substitution of $\eta^5$-Pyrrolyl Ligands in Ruthenium (II) Complexes" *Organometallics*, 1997, 16, 2325-2344.
Beatrice Vendemiati et al., "Paramagnetic Bis (amidinate) Iron (II) Complexes and their Diamagnetic Dicarbonyl Derivatives", *Eur. J. Inorg. Chem.* 2001, 707-711.
Booyong S. Lim et al., "Synthesis and Characterization of Volatile, Thermally Stable, Reactive Transition Metal Amidinates", *Inorg, Chem.*, PREFRINT.

* cited by examiner

*Primary Examiner*—Melvin C Mayes
*Assistant Examiner*—James Corno
(74) *Attorney, Agent, or Firm*—Iurie A. Schwartz

(57) ABSTRACT

This invention relates to processes for the production of organometallic compounds represented by the formula $M(L)_3$ wherein M is a Group VIII metal, e.g., ruthenium, and L is the same or different and represents a substituted or unsubstituted amidinato group or a substituted or unsubstituted amidinato-like group, which process comprises (i) reacting a substituted or unsubstituted metal source compound, e.g., ruthenium (II) compound, with a substituted or unsubstituted amidinate or amidinate-like compound in the presence of a solvent and under reaction conditions sufficient to produce a reaction mixture comprising said organometallic compound, e.g., ruthenium (III) compound, and (ii) separating said organometallic compound from said reaction mixture. The organometallic compounds are useful in semiconductor applications as chemical vapor or atomic layer deposition precursors for film depositions.

9 Claims, No Drawings

PROCESSES FOR THE PRODUCTION OF ORGANOMETALLIC COMPOUNDS

FIELD OF THE INVENTION

This invention relates to processes for producing organometallic amidinate compounds, a method for producing a film or coating from the organometallic amidinate compounds, and ruthenium amidinate compounds that are hydrogen reducible and deposit in a self-limiting manner. The organometallic amidinate compounds are useful in semiconductor applications as chemical vapor or atomic layer deposition precursors for film depositions.

BACKGROUND OF THE INVENTION

In existing semiconductor devices, transistors communicate with one another via an elaborate series of copper interconnects connected through a series of metal layers above the transistor. To minimize the capacitive coupling between these interconnects, the space between is occupied by a material with a low dielectric constant (i.e., low-K materials). To prevent the diffusion of copper into this low-K material, a composite barrier is put in place. Current practices use physical vapor deposition techniques to accomplish this. An example of a BEOL (back end of the line) interconnects strategy for putting a barrier in place by physical vapor deposition and electrochemical deposition is as follows: low K repair, tantalum nitride reactive sputter physical vapor deposition, tantalum sputter physical vapor deposition, copper seed sputter physical vapor deposition and copper electrochemical deposition.

Physical vapor deposition techniques result in anisotropic deposition, with the thickness of the film on sidewalls being significantly thinner than the thickness of the film on the horizontal surfaces of the wafer. Since the ability of the barrier to prevent the migration of copper through to the low-K dielectric is proportional to the thickness of the barrier, the barrier is thicker than it needs to be on the horizontal wafer surfaces.

As the semiconductor moves to future technology nodes, the dimensions of interconnects will decrease. This will result in a decrease of the surface area to volume ratio of the interconnect, concomitant with an increase in the volume occupied by the diffusion barrier. As the barrier occupies more of the interconnect channel space, the effective resistivity of the interconnect increases for two reasons: first, decrease in the size of the interconnect and second, copper/barrier surface scattering of electrons becomes a more critical issue.

One method of minimizing these issues is to deposit films isotropically using atomic layer deposition. Unfortunately, no chemistries exist that can deposit tantalum metal using atomic layer deposition. The role of tantalum in the deposition strategy described above is to generate adequate adhesion between the copper seed and tantalum nitride. Without tantalum, copper delaminates from the tantalum nitride film compromising device performance.

Another metal that may be viable within this application is ruthenium. Ruthenium is adherent to titanium nitride and thus one may expect that it would be adherent to tantalum nitride, moreover, the use of ruthenium could obviate the requirement of a copper seed layer since ruthenium has sufficient conductivity that copper electrochemical deposition could be carried out directly on a ruthenium film. An isotropic atomic layer deposition strategy for forming BEOL interconnects using ruthenium is as follows: low K repair, tantalum nitride atomic layer deposition, ruthenium atomic layer deposition and copper electrochemical deposition.

While there have been reports in the literature detailing ruthenium atomic layer deposition, all of them involve the use of either oxygen or a plasma. Oxygen based chemistries are incompatible with a BEOL integration sequence since the presence of trace amounts of oxygen within the deposited film could diffuse into the copper channel resulting in the formation of copper oxides compromising device performance. Similarily, concerns exist regarding the ability of plasmas to deposit isotropic films.

Ideally, a suitable BEOL atomic layer deposition process would be capable of using hydrogen, or other reducing gas, at temperatures below 300° C. so that the deposition could be carried out in a manner compatible with the rest of the BEOL integration strategy. In addition to being hydrogen reducible, chemistries should deposit in a self-limiting manner. In other words, in the absence of a reactant gas, the substrate should saturate with a monolayer, or fraction of a monolayer, of a dissociatively chemisorbed precursor.

The problem is that there are no known suitable hydrogen reducible ruthenium complexes of sufficient volatility for use as atomic layer deposition precursors, and as such, no self-limiting, hydrogen reducible precursors have been identified. It would therefore be desirable in the art to develop self-limiting, hydrogen reducible ruthenium complexes suitable for BEOL atomic layer deposition processes.

Further, the synthetic processes utilized to generate organometallic precursors are highly important, and must insure safety, high purity, throughput, and consistency. The economics associated with such processes together with the rigid requirements of the electronics industry make the synthesis of organometallic precursors challenging. Developing a methodology for producing organometallic precursors that addresses the aforementioned potential hold-ups would be beneficial toward establishing the production of these materials for use in the electronics industry.

Processes for preparing organometallic compounds include those disclosed in U.S. Patent Application Publication No. US 2004/0127732 A1, published Jul. 1, 2004. Organometallic precursor compounds may also be prepared by processes such as described in Vendemiati, Beatrice et al., Paramagnetic Bis(amidinate)Iron(II) Complexes and their Diamagnetic Dicarbonyl Derivatives, Euro. J. Inorg. Chem. 2001, 707-711; Lim, Booyong S. et al., Synthesis and Characterization of Volatile, Thermally Stable, Reactive Transition Metal Amidinates, Inorg. Chem., 2003, Preprint; and references therein.

A need exists for new processes for making organometallic precursors that give higher product yields, operate efficiently, provide consistency and permit easier scale up for production quantities of organometallic compounds. It would therefore be desirable in the art to provide new processes for making organometallic compounds that address these needs.

Also, in developing methods for forming thin films by chemical vapor deposition or atomic layer deposition methods, precursors that preferably are hydrogen reducible, deposit in a self-limiting manner, liquid at room temperature, have adequate vapor pressure, have appropriate thermal stability (i.e., for chemical vapor deposition will decompose on the heated substrate but not during delivery, and for atomic layer deposition will not decompose thermally but will react when exposed to co-reactant), can form uniform films, and will leave behind very little, if any, undesired impurities (e.g., halides, carbon, etc.) are highly desirable. A need exists for developing new compounds and for exploring their potential as chemical vapor or atomic layer deposition precursors for film depositions, in particular self-limiting, hydrogen reducible organometallic complexes for atomic layer deposition as indicated above. It would therefore be desirable in the art to provide precursors that possess some, or preferably all, of the above characteristics.

SUMMARY OF THE INVENTION

This invention relates to processes for the production of organometallic compounds selected from the following:

(1) a process for the production of an organometallic compound represented by the formula $(L)_2M(L')_2$ which process comprises (i) reacting a substituted or unsubstituted metal source compound represented by the formula $MX_2R$ with a substituted or unsubstituted amidinate or amidinate-like compound represented by the formula $A_1L$ and a ligand source represented by the formula L', in the presence of a solvent and under reaction conditions sufficient to produce a reaction mixture comprising said organometallic compound, and (ii) separating said organometallic compound from said reaction mixture; and (2) a process for the production of an organometallic compound represented by the formula $M(L)_3$ which process comprises (i) reacting a substituted or unsubstituted metal source compound represented by the formula $MX_2R$, e.g., ruthenium (II) compound, with a substituted or unsubstituted amidinate or amidinate-like compound represented by the formula $A_1L$ in the presence of a solvent and under reaction conditions sufficient to produce a reaction mixture comprising said organometallic compound, e.g., ruthenium (III) compound, and (ii) separating said organometallic compound from said reaction mixture;

wherein M is a Group VIII metal, X is a halogen group, R is a substituted or unsubstituted hydrocarbon group, $A_1$ is an alkali metal, L is the same or different and represents a substituted or unsubstituted amidinato group or a substituted or unsubstituted amidinato-like group, and L' is the same or different and represents $N_2$ or a substituted or unsubstituted heteroatom-containing group.

This invention also relates to organometallic ruthenium compounds represented by the formula

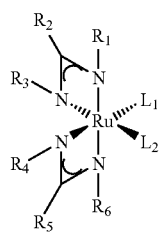

wherein $R_1$, $R_2$, $R_3$, $R_4$, $R_5$ and $R_6$ are the same or different and each represents hydrogen, a halogen atom, an acyl group having from 1 to about 12 carbon atoms, preferably from 1 to about 6 carbon atoms, an alkoxy group having from 1 to about 12 carbon atoms, an alkoxycarbonyl group having from 1 to about 12 carbon atoms, preferably from 1 to about 6 carbon atoms, an alkyl group having from 1 to about 12 carbon atoms, preferably from 1 to about 6 carbon atoms, an amine group having from 1 to about 12 carbon atoms, preferably from 1 to about 6 carbon atoms, or a silyl group having from 0 to about 12 carbon atoms, preferably from 0 to about 6 carbon atoms, and $L_1$ and $L_2$ are the same or different and each represents $N_2$ or a substituted or unsubstituted heteroatom-containing group. The organometallic ruthenium compounds are preferably hydrogen reducible and deposit in a self-limiting manner.

This invention further relates to a method for producing a film, coating or powder by decomposing an organometallic precursor compound represented by the formula $(L)_2M(L')_2$ above, thereby producing the film, coating or powder. Typically, the decomposing of said organometallic precursor compound is thermal, chemical, photochemical or plasma-activated. Film deposition is preferably self-limiting and conducted in the presence of at least one reactive gas such as hydrogen.

This invention also relates to organometallic precursor mixtures comprising (i) a first organometallic precursor compound represented by the formula $(L)_2M(L')_2$ or $M(L)_3$ above, and (ii) one or more different organometallic precursor compounds (e.g., a hafnium-containing, tantalum-containing or molybdenum-containing organometallic precursor compound).

This invention relates in particular to depositions involving amidinate-based ruthenium precursors. These precursors may have advantages over the other known precursors, especially when utilized in tandem with other 'next-generation' materials (e.g., hafnium, tantalum and molybdenum). These ruthenium-containing materials can be used for a variety of purposes such as dielectrics, barriers, and electrodes, and in many cases show improved properties (thermal stability, desired morphology, less diffusion, lower leakage, less charge trapping, and the like) than the non-ruthenium containing films. These amidinate-based ruthenium precursors may be deposited by atomic layer deposition employing a hydrogen reduction pathway in a self-limiting manner, thereby enabling use of ruthenium as a barrier/adhesion layer in conjunction with tantalum nitride in BEOL liner applications. Such amidinate-based ruthenium precursors deposited in a self-limiting manner by atomic layer deposition may enable conformal film growth over high aspect ratio trench architectures in a reducing environment.

The invention has several advantages. For example, the processes of the invention are useful in generating organometallic compound precursors that have varied chemical structures and physical properties. Films generated from the organometallic compound precursors can be deposited in a self-limiting manner with a short incubation time, and the films deposited from the organometallic compound precursors exhibit good smoothness.

This invention relates in particular to chemical vapor deposition and atomic layer deposition precursors for next generation devices, specifically amidinate-containing ruthenium precursors that are self-limiting, hydrogen reducible and are desirably liquid at room temperature, i.e., 20° C.

DETAILED DESCRIPTION OF THE INVENTION

As indicated above, this invention relates to processes for the production of organometallic compounds selected from the following:

(1) a process for the production of an organometallic compound represented by the formula $(L)_2M(L')_2$ which process comprises (i) reacting a substituted or unsubstituted metal source compound represented by the formula $MX_2R$ with a substituted or unsubstituted amidinate or amidinate-like compound represented by the formula $A_1L$ and a ligand source represented by the formula L', in the presence of a solvent and under reaction conditions sufficient to produce a reaction mixture comprising said organometallic compound, and (ii) separating said organometallic compound from said reaction mixture; and (2) a process for the production of an organometallic compound represented by the formula $M(L)_3$ which process comprises (i) reacting a substituted or unsubstituted metal source compound represented by the formula $MX_2R$ with a substituted or unsubstituted amidinate or amidinate-like compound represented by the formula $A_1L$ in the presence of a solvent and under reaction conditions sufficient to produce a reaction mixture comprising said organometallic compound, and (ii) separating said organometallic compound from said reaction mixture;

wherein M is a Group VIII metal, X is a halogen group, R is a substituted or unsubstituted hydrocarbon group, $A_1$ is an alkali metal, L is the same or different and represents a substituted or unsubstituted amidinato group or a substituted or unsubstituted amidinato-like group, and L' is the same or different and represents $N_2$ or a substituted or unsubstituted heteroatom-containing group.

The metal source compound starting material $MX_2R$ may be selected from a wide variety of compounds known in the art. The invention herein most prefers metals selected from Ru, Os and Fe. Illustrative metal source compounds represented by the formula $MX_2R$ include, for example, bis[dichloro($\eta^6$-benzene)ruthenium (II)], bis[dichloro($\eta^6$-toluene)ruthenium (II)], and the like. As indicated above, M is a Group VIII metal such as Ru, Os or Fe, X is a halogen group such as fluoro, chloro, bromo and iodo, and R is a substituted or unsubstituted hydrocarbon group, preferably an unsaturated hydrocarbon group, more preferably an aromatic compound such as $\eta^6$-benzene, $\eta^6$-toluene, and the like.

In a preferred embodiment of process (1) above, a ruthenium (II) source starting material, e.g., bis[dichloro($\eta^6$-benzene)ruthenium (II)], can be reacted with an amidinate starting material, e.g., lithium (N,N'-diisopropylacetamidinate), and nitrogen gas to give a ruthenium (II) amidinate product, e.g., bis Q(N,N'-diisopropylacetamidinato)dinitrogenruthenium (II). In a preferred embodiment of process (2) above, a ruthenium (II) source starting material, e.g., bis[dichloro($\eta^6$-benzene)ruthenium (II)], can be reacted with an amidinate starting material, e.g., lithium (N,N'-diisopropylacetamidinate), to give a ruthenium (III) amidinate product, e.g., tris (N,N'-diisopropylacetamidinato)ruthenium (III).

The process of the invention is preferably useful in generating organometallic ruthenium compound precursors that have varied chemical structures and physical properties. A wide variety of reaction materials may be employed in the processes of this invention. For example, in the preparation of the metal source compounds, ruthenium starting materials that may be used include commercial grade Ru(III) chloride hydrate, $\alpha$-ruthenium(III) chloride, $\beta$-ruthenium(III) chloride, ruthenium(III) nitrate, $(PPh_3)_xRuCl_2$ (x=3-4) and the like.

The concentration of the metal source compound starting material can vary over a wide range, and need only be that minimum amount necessary to react with the amidinate or amidinate-like compound and ligand source in process (1) above or the amidinate or amidinate-like compound in process (2) above, and to provide the given metal concentration desired to be employed and which will furnish the basis for at least the amount of metal necessary for the organometallic compounds of this invention. In general, depending on the size of the reaction mixture, metal source compound starting material concentrations in the range of from about 1 millimole or less to about 10,000 millimoles or greater, should be sufficient for most processes.

The amidinate or amidinate-like compound starting material $A_1L$ may be selected from a wide variety of compounds known in the art. Illustrative amidinate compounds represented by the formula $A_1L$ include lithium amidinates such as lithium (N,N'-diisopropylacetamidinate), lithium (N,N'-diisopropylformamidinate), lithium (N,N'-di-n-propylformamidinate), lithium (N,N'-di-n-propylacetamidinate), lithium (N,N'-diethylacetamidinate), lithium (N,N'-diethylformamidinate), lithium (N,N'-dimethylacetamidinate), lithium (N,N'-dimethylformamidinate), sodium amidinates above, bromomagnesium amidinates above, and the like. Illustrative amidinate-like compounds represented by the formula $A_1L$ include negatively charged, chelating, four electron donor compounds such as lithium beta-diketonates, lithium allyls, lithium dithiocarbamates, sodium amidinate-like compounds above, bromomagnesium amidinate-like compounds above, and the like. Schiff bases and certain chelating alkylamines and arylamines such as 2-[(dimethylamino)methyl]phenyl are illustrative nitrogen bound negatively charged, chelating, four electron donor compounds. As indicated above, $A_1$ is an alkali metal such as lithium, sodium and bromium and L is the same or different and represents a substituted or unsubstituted amidinato group or a substituted or unsubstituted amidinato-like group.

The concentration of the amidinate or amidinate-like compound starting material can vary over a wide range, and need only be that minimum amount necessary to react with the metal source compound and ligand source in process (1) above or the metal source compound in process (2) above. In general, depending on the size of the first reaction mixture, amidinate or amidinate-like compound starting material concentrations in the range of from about 1 millimole or less to about 10,000 millimoles or greater, should be sufficient for most processes.

The ligand source starting material L' may be selected from a wide variety of compounds known in the art. The invention herein most prefers ligand source starting materials selected from $N_2$, $NCR_7$, $PR_7R_8R_9$ or $NR_7R_8R_9$, wherein $R_7$, $R_8$ and $R_9$ are the same or different and each represents hydrogen, a halogen atom, an acyl group having from 1 to about 12 carbon atoms, preferably from 1 to about 6 carbon atoms, an alkoxy group having from 1 to about 12 carbon atoms, preferably from 1 to about 6 carbon atoms, an alkoxycarbonyl group having from 1 to about 12 carbon atoms, preferably from 1 to about 6 carbon atoms, an alkyl group having from 1 to about 12 carbon atoms, preferably from 1 to about 6 carbon atoms, an amine group having from 1 to about 12 carbon atoms, preferably from 1 to about 6 carbon atoms, or a silyl group having from 0 to about 12 carbon atoms, preferably from 0 to about 6 carbon atoms. Illustrative ligand source starting materials represented by the formula L' include, for example, two electron donor ligands such as nitriles, dinitrogen, amines, low molecular weight phosphines, and the like. As indicated above, L' is the same or different and represents $N_2$ or a substituted or unsubstituted heteroatom-containing group.

The concentration of the ligand source starting material can vary over a wide range, and need only be that minimum amount necessary to react with the metal source compound and amidinate or amidinate-like compound in process (1) above. In general, depending on the size of the reaction mixture, ligand source starting material concentrations in the range of from about 1 millimole or less to about 10,000 millimoles or greater, should be sufficient for most processes.

The ligand source material may also be used in process (2) above in amounts that it would not be expected to coordinate directly to the transition metal. However, if the ligand source material is used in sufficient amounts in process (2) above, it is expected that organometallic compounds represented by the formula $(L)_2M(L')_2$ along with organometallic compounds represented by the formula $M(L)_3$ may be produced. Likewise, if the ligand source material is used in insufficient amounts in process (1) above, it is expected that organometallic compounds represented by the formula M(L)$_3$ along with organometallic compounds represented by the formula (L)$_2$M(L')$_2$ may be produced.

Permissible substituents of the substituted amidinate and amidinate-like groups (L), the substituted hydrocarbon groups (R) and the substituted heteroatom-containing groups (L', L$_1$ and L$_2$) include halogen atoms, acyl groups having from 1 to about 12 carbon atoms, alkoxy groups having from 1 to about 12 carbon atoms, alkoxycarbonyl groups having from 1 to about 12 carbon atoms, alkyl groups having from 1 to about 12 carbon atoms, amine groups having from 1 to about 12 carbon atoms or silyl groups having from 0 to about 12 carbon atoms.

Illustrative halogen atoms include, for example, fluorine, chlorine, bromine and iodine. Preferred halogen atoms include chlorine and fluorine.

Illustrative acyl groups include, for example, formyl, acetyl, propionyl, butyryl, isobutyryl, valeryl, 1-methylpropylcarbonyl, isovaleryl, pentylcarbonyl, 1-methylbutylcarbonyl, 2-methylbutylcarbonyl, 3-methylbutylcarbonyl, 1-ethylpropylcarbonyl, 2-ethylpropylcarbonyl, and the like. Preferred acyl groups include formyl, acetyl and propionyl.

Illustrative alkoxy groups include, for example, methoxy, ethoxy, n-propoxy, isopropoxy, n-butoxy, isobutoxy, sec-butoxy, tert-butoxy, pentyloxy, 1-methylbutyloxy, 2-methylbutyloxy, 3-methylbutyloxy, 1,2-dimethylpropyloxy, hexyloxy, 1-methylpentyloxy, 1-ethylpropyloxy, 2-methylpentyloxy, 3-methylpentyloxy, 4-methylpentyloxy, 1,2-dimethylbutyloxy, 1,3-dimethylbutyloxy, 2,3-dimethylbutyloxy, 1,1-dimethylbutyloxy, 2,2-dimethylbutyloxy, 3,3-dimethylbutyloxy, and the like. Preferred alkoxy groups include methoxy, ethoxy and propoxy.

Illustrative alkoxycarbonyl groups include, for example, methoxycarbonyl, ethoxycarbonyl, propoxycarbonyl, isopropoxycarbonyl, cyclopropoxycarbonyl, butoxycarbonyl, isobutoxycarbonyl, sec-butoxycarbonyl, tert-butoxycarbonyl, and the like. Preferred alkoxycarbonyl groups include methoxycarbonyl, ethoxycarbonyl, propoxycarbonyl, isopropoxycarbonyl and cyclopropoxycarbonyl.

Illustrative alkyl groups include, for example, methyl, ethyl, n-propyl, isopropyl, n-butyl, isobutyl, sec-butyl, tert-butyl, pentyl, isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, cyclopropylmethyl, cyclopropylethyl, cyclobutylmethyl, and the like. Preferred alkyl groups include methyl, ethyl, n-propyl, isopropyl and cyclopropyl.

Illustrative amine groups include, for example, methylamine, dimethylamine, ethylamine, diethylamine, propylamine, dipropylamine, isopropylamine, diisopropylamine, butylamine, dibutylamine, tert-butylamine, di(tert-butyl)amine, ethylmethylamine, butylmethylamine, cyclohexylamine, dicyclohexylamine, and the like. Preferred amine groups include dimethylamine, diethylamine and diisopropylamine.

Illustrative silyl groups include, for example, silyl, trimethylsilyl, triethylsilyl, tris(trimethylsilyl)methyl, trisilylmethyl, methylsilyl and the like. Preferred silyl groups include silyl, trimethylsilyl and triethylsilyl.

Illustrative organometallic precursor compounds that can be made by process (1) of this invention include, for example, bis(N,N'-diisopropylacetamidinato)dinitrogenruthenium (II), bis(N,N'-diisopropylacetamidinato)di-trimethylphosphineruthenium (II), bis(N,N'-diisopropylformamidinato)dinitrogenruthenium (II), bis(N,N'-diisopropylformamidinato)di-trimethylphosphineruthenium (II), bis(N,N'-di-n-propylacetamidinato)dinitrogenruthenium (II), bis(N,N'-di-n-propylacetamidinato)di-trimethylphosphineruthenium (II), bis(N,N'-di-n-propylformamidinato)dinitrogenruthenium (II), bis(N,N'-di-n-propylformamidinato)di-trimethylphosphineruthenium (II), bis(N,N'-diethylacetamidinato)dinitrogenruthenium (II), bis(N,N'-diethylacetamidinato)di-trimethylphosphineruthenium (II), bis(N,N'-diethylformamidinato)dinitrogenruthenium (II), bis(N,N'-diethylformamidinato)di-trimethylphosphineruthenium (II), bis(N,N'-dimethylacetamidinato)dinitrogenruthenium (II), bis(N,N'-dimethylacetamidinato)di-trimethylphosphineruthenium (II), bis(N,N'-dimethylformamidinato)dinitrogenruthenium (II), bis(N,N'-dimethylformamidinato)di-trimethylphosphineruthenium (II), and the like. In a preferred embodiment of process (1) of this invention, a ruthenium (II) source starting material, e.g., bis[dichloro($\eta^6$-benzene)ruthenium (II)], can be reacted with an amidinate starting material, e.g., lithium (N,N'-diisopropylacetamidinate), and nitrogen gas to give a ruthenium (II) amidinate product, e.g., bis(N,N'-diisopropylacetamidinato)dinitrogenruthenium (II).

Illustrative organometallic precursor compounds that can be made by process (2) of this invention include, for example, tris(N,N'-diisopropylacetamidinato)ruthenium (III), tris(N,N'-diisopropylformamidinato)ruthenium (III), tris(N,N'-di-n-propylacetamidinato)ruthenium (III), tris(N,N'-di-n-propylformamidinato)ruthenium (III), tris(N,N'-diethylacetamidinato)ruthenium (III), tris(N,N'-diethylformamidinato)ruthenium (III), tris(N,N'-dimethylacetamidinato)ruthenium (III), tris(N,N'-dimethylformamidinato)ruthenium (III), and the like. In a preferred embodiment of process (2) of this invention, a ruthenium (II) source starting material, e.g., bis[dichloro($\eta^6$-benzene)ruthenium (II)], can be reacted with an amidinate starting material, e.g., lithium (N,N'-diisopropylacetamidinate), to give a ruthenium (III) amidinate product, e.g., tris (N,N'-diisopropylacetamidinato)ruthenium (III).

The processes are particularly well-suited for large scale production since they can be conducted using the same equipment, some of the same reagents and process parameters that can easily be adapted to manufacture a wide range of products. The processes provide for the synthesis of organometallic precursor compounds using processes where all manipulations can be carried out in a single vessel, and which route to the organometallic precursor compounds does not require the isolation of the metal source compound starting material or an intermediate complex.

The solvent employed in the process of this invention may be any saturated and unsaturated hydrocarbons, aromatic hydrocarbons, aromatic heterocycles, alkyl halides, silylated hydrocarbons, ethers, polyethers, thioethers, esters, thioesters, lactones, amides, amines, polyamines, nitrites, silicone oils, other aprotic solvents, or mixtures of one or more of the above; more preferably, diethylether, pentanes, or dimethoxyethanes; and most preferably hexanes or THF. Any suitable solvent which does not unduly adversely interfere with the intended reaction can be employed. Mixtures of one or more different solvents may be employed if desired. The amount of solvent employed is not critical to the subject invention and need only be that amount sufficient to solubilize the reaction components in the reaction mixture. In general, the amount of solvent may range from about 5 percent by weight up to about 99 percent by weight or more based on the total weight of the reaction mixture starting materials.

Reaction conditions for the reaction of the amidinate compound with the metal source compound and ligand source starting material, (i.e., process (1) above) such as temperature, pressure and contact time, may also vary greatly and any suitable combination of such conditions may be employed herein. The reaction temperature may be the reflux temperature of any of the aforementioned solvents, and more preferably between about −80° C. to about 150° C., and most preferably between about 20° C. to about 80° C. Normally the reaction is carried out under ambient pressure and the contact time may vary from a matter of seconds or minutes to a few hours or greater. The reactants can be added to the reaction mixture or combined in any order. The stir time employed can range from about 0.1 to about 400 hours, preferably from about 1 to 75 hours, and more preferably from about 4 to 16 hours, for all steps.

Reaction conditions for the reaction of the amidinate compound with the metal source compound (i.e., process (2) above) such as temperature, pressure and contact time, may also vary greatly and any suitable combination of such conditions may be employed herein. The reaction temperature may be the reflux temperature of any of the aforementioned solvents, and more preferably between about −80° C. to about 150° C., and most preferably between about 20° C. to about 80° C. Normally the reaction is carried out under ambient pressure and the contact time may vary from a matter of seconds or minutes to a few hours or greater. The reactants can be added to the reaction mixture or combined in any order. The stir time employed can range from about 0.1 to about 400 hours, preferably from about 1 to 75 hours, and more preferably from about 4 to 16 hours, for all steps.

Other alternative processes that may be used in preparing the organometallic ruthenium compounds of this invention include those disclosed in U.S. Patent Application Publication No. US 2004/0127732 A1, published Jul. 1, 2004, the disclosure of which is incorporated herein by reference. The organometallic precursor compounds of this invention may also be prepared by conventional processes such as described in Vendemiati, Beatrice et al., Paramagnetic Bis(amidinate) Iron(II) Complexes and their Diamagnetic Dicarbonyl Derivatives, Euro. J. Inorg. Chem. 2001, 707-711; Lim, Booyong S. et al., Synthesis and Characterization of Volatile, Thermally Stable, Reactive Transition Metal Amidinates, Inorg. Chem., 2003, Preprint; and references therein.

For organometallic precursor compounds prepared by the processes of this invention, purification can occur through recrystallization, more preferably through extraction of reaction residue (e.g., hexane) and chromatography, and most preferably through sublimation and distillation.

Those skilled in the art will recognize that numerous changes may be made to the processes described in detail herein, without departing in scope or spirit from the present invention as more particularly defined in the claims below.

Examples of techniques that can be employed to characterize the organometallic precursor compounds formed by the synthetic processes described above include, but are not limited to, analytical gas chromatography, nuclear magnetic resonance, thermogravimetric analysis, inductively coupled plasma mass spectrometry, differential scanning calorimetry, vapor pressure and viscosity measurements.

The rate of vaporization, which correlates well with vapor pressure of organometallic compound precursors described above within the confines of the experiment, can be measured by thermogravimetric analysis techniques known in the art. Equilibrium vapor pressures also can be measured, for example by evacuating all gases from a sealed vessel, after which vapors of the compounds are introduced to the vessel and the pressure is measured as known in the art.

As indicated above, this invention also relates to organometallic ruthenium precursor compounds represented by the formula

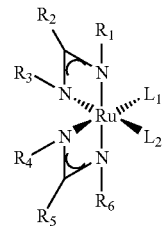

wherein $R_1$, $R_2$, $R_3$, $R_4$, $R_5$ and $R_6$ are the same or different and each represents hydrogen, a halogen atom, an acyl group having from 1 to about 12 carbon atoms, preferably from 1 to about 6 carbon atoms, an alkoxy group having from 1 to about 12 carbon atoms, preferably from 1 to about 6 carbon atoms, an alkoxycarbonyl group having from 1 to about 12 carbon atoms, preferably from 1 to about 6 carbon atoms, an alkyl group having from 1 to about 12 carbon atoms, preferably from 1 to about 6 carbon atoms, an amine group having from 1 to about 12 carbon atoms, preferably from 1 to about 6 carbon atoms, or a silyl group having from 0 to about 12 carbon atoms, preferably from 0 to about 6 carbon atoms, and $L_1$ and $L_2$ are the same or different and each represents $N_2$ or a substituted or unsubstituted heteroatom-containing group. Illustrative such groups are set forth above.

Illustrative organometallic ruthenium precursor compounds represented by the above formula include bis(N,N'-diisopropylacetamidinato)dinitrogenruthenium (II), bis(N,N'diisopropylacetamidinato)di-trimethylphosphineruthenium (II), bis(N,N'-diisopropylformamidinato)dinitrogenruthenium (II), bis(N,N'-diisopropylformamidinato)di-trimethylphosphineruthenium (II), bis(N,N'-di-n-propylacetamidinato)dinitrogenruthenium (II), bis(N,N'-di-n-propylacetamidinato)di-trimethylphosphineruthenium (II), bis(N,N'-di-n-propylformamidinato)dinitrogenruthenium (II), bis(N,N'-di-n-propylformamidinato)di-trimethylphosphineruthenium (II), bis(N,N'-diethylacetamidinato)dinitrogenruthenium (II), bis(N,N'-diethylacetamidinato)di-trimethylphosphineruthenium (II), bis(N,N'-diethylformamidinato)dinitrogenruthenium (II), bis(N,N'-diethylformamidinato)di-trimethylphosphineruthenium (II), bis(N,N'-dimethylacetamidinato)dinitrogenruthenium (II), bis(N,N'-dimethylacetamidinato)di-trimethylphosphineruthenium (II), bis(N,N'-dimethylformamidinato)dinitrogenruthenium (II), and bis(N,N'-dimethylformamidinato)di-trimethylphosphineruthenium (II).

The organometallic compound precursors described herein are preferably hydrogen reducible, deposit in a self-limiting manner, liquid at room temperature, i.e., 20° C., and are well suited for preparing in-situ powders and coatings. For instance, a liquid organometallic compound precursor can be applied to a substrate and then heated to a temperature sufficient to decompose the precursor, thereby forming a metal or metal oxide coating on the substrate. Applying a liquid precursor to the substrate can be by painting, spraying, dipping or by other techniques known in the art. Heating can be conducted in an oven, with a heat gun, by electrically heating the substrate, or by other means, as known in the art. A layered coating can be obtained by applying an organometallic compound precursor, and heating and decomposing it, thereby forming a first layer, followed by at least one other coating with the same or different precursors, and heating.

Liquid organometallic compound precursors such as described above also can be atomized and sprayed onto a substrate. Atomization and spraying means, such as nozzles, nebulizers and others, that can be employed are known in the art.

In preferred embodiments of the invention, an organometallic compound, such as described above, is employed in gas phase deposition techniques for forming powders, films or coatings. The compound can be employed as a single source precursor or can be used together with one or more other precursors, for instance, with vapor generated by heating at least one other organometallic compound or metal complex. More than one organometallic compound precursor, such as described above, also can be employed in a given process.

As indicated above, this invention relates to organometallic precursor mixtures comprising (i) a first organometallic precursor compound represented by the formula $(L)_2M(L')_2$ or $M(L)_3$ above and (ii) one or more different organometallic precursor compounds (e.g., a hafnium-containing, tantalum-containing or molybdenum-containing organometallic precursor compound).

Deposition can be conducted in the presence of other gas phase components. In an embodiment of the invention, film deposition is conducted in the presence of at least one non-reactive carrier gas. Examples of non-reactive gases include inert gases, e.g., nitrogen, argon, helium, as well as other gases that do not react with the organometallic compound precursor under process conditions. In other embodiments, film deposition is conducted in the presence of at least one reactive gas. Some of the reactive gases that may be employed include but are not limited to hydrazine, oxygen, hydrogen, air, oxygen-enriched air, ozone ($O_3$), nitrous oxide ($N_2O$), water vapor, organic vapors, ammonia and others. As known in the art, the presence of an oxidizing gas, such as, for example, air, oxygen, oxygen-enriched air, $O_3$, $N_2O$ or a vapor of an oxidizing organic compound, favors the formation of a metal oxide film.

In an embodiment, hydrogen or another reducing gas may be used in a BEOL atomic layer deposition process at temperatures below 300° C. so that the deposition can be carried out in a manner compatible with the rest of the BEOL integration strategy. Hydrogen reducible ruthenium complexes may also be used for the integration of ruthenium in MIM stacked cell DRAM capacitors.

In addition to being hydrogen reducible, the ruthenium complexes of this invention deposit in a self-limiting manner. For example, in the absence of a reactant gas, the substrate becomes saturated with a monolayer, or fraction of a monolayer, of the dissociatively chemisorbed ruthenium precursor. In a self-limiting deposition, only one layer of organometallic precursor is deposited at a time. Amidinate-based ruthenium precursors deposited in a self-limiting manner by atomic layer deposition may enable conformal film growth over high aspect ratio trench architectures in a reducing environment.

As indicated above, this invention also relates in part to a method for producing a film, coating or powder. The method includes the step of decomposing at least one organometallic compound precursor, thereby producing the film, coating or powder, as further described below.

Deposition methods described herein can be conducted to form a film, powder or coating that includes a single metal or a film, powder or coating that includes a single metal oxide. Mixed films, powders or coatings also can be deposited, for instance mixed metal oxide films. A mixed metal oxide film can be formed, for example, by employing several organometallic precursors, at least one of which being selected from the organometallic compounds described above.

Gas phase film deposition can be conducted to form film layers of a desired thickness, for example, in the range of from about 1 nm to over 1 mm. The precursors described herein are particularly useful for producing thin films, e.g., films having a thickness in the range of from about 10 nm to about 100 nm. Films of this invention, for instance, can be considered for fabricating metal electrodes, in particular as n-channel metal electrodes in logic, as capacitor electrodes for DRAM applications, and as dielectric materials.

The method also is suited for preparing layered films, wherein at least two of the layers differ in phase or composition. Examples of layered film include metal-insulator-semiconductor, and metal-insulator-metal.

In an embodiment, the invention is directed to a method that includes the step of decomposing vapor of an organometallic compound precursor described above, thermally, chemically, photochemically or by plasma activation, thereby forming a film on a substrate. For instance, vapor generated by the compound is contacted with a substrate having a temperature sufficient to cause the organometallic compound to decompose and form a film on the substrate.

The organometallic compound precursors can be employed in chemical vapor deposition or, more specifically, in metalorganic chemical vapor deposition processes known in the art. For instance, the organometallic compound precursors described above can be used in atmospheric, as well as in low pressure, chemical vapor deposition processes. The compounds can be employed in hot wall chemical vapor deposition, a method in which the entire reaction chamber is heated, as well as in cold or warm wall type chemical vapor deposition, a technique in which only the substrate is being heated.

The organometallic compound precursors described above also can be used in plasma or photo-assisted chemical vapor deposition processes, in which the energy from a plasma or electromagnetic energy, respectively, is used to activate the chemical vapor deposition precursor. The compounds also can be employed in ion-beam, electron-beam assisted chemical vapor deposition processes in which, respectively, an ion beam or electron beam is directed to the substrate to supply energy for decomposing a chemical vapor deposition precursor. Laser-assisted chemical vapor deposition processes, in which laser light is directed to the substrate to affect photolytic reactions of the chemical vapor deposition precursor, also can be used.

The method of the invention can be conducted in various chemical vapor deposition reactors, such as, for instance, hot or cold-wall reactors, plasma-assisted, beam-assisted or laser-assisted reactors, as known in the art.

Examples of substrates that can be coated employing the method of the invention include solid substrates such as metal substrates, e.g., Al, Ni, Ti, Co, Pt, Ta; metal silicides, e.g., $TiSi_2$, $CoSi_2$, $NiSi_2$; semiconductor materials, e.g., Si, SiGe, GaAs, InP, diamond, GaN, SiC; insulators, e.g., $SiO_2$, $Si_3N_4$, $HfO_2$, $HfSiO_2$, HfSiON, $Ta_2O_5$, $Al_2O_3$, barium strontium titanate (BST); barrier materials, e.g., TiN, TaN, WN, WSiN, TaSiN; or on substrates that include combinations of materials. In addition, films or coatings can be formed on glass, ceramics, plastics, thermoset polymeric materials, and on other coatings or film layers. In preferred embodiments, film deposition is on a substrate used in the manufacture or processing of electronic components. In other embodiments, a substrate is employed to support a low resistivity conductor deposit that is stable in the presence of an oxidizer at high temperature or an optically transmitting film.

The method of this invention can be conducted to deposit a film on a substrate that has a smooth, flat surface. In an embodiment, the method is conducted to deposit a film on a substrate used in wafer manufacturing or processing. For instance, the method can be conducted to deposit a film on patterned substrates that include features such as trenches, holes or vias. Furthermore, the method of the invention also can be integrated with other steps in wafer manufacturing or processing, e.g., masking, etching and others.

Chemical vapor deposition films can be deposited to a desired thickness. For example, films formed can be less than 1 micron thick, preferably less than 500 nanometers and more preferably less than 200 nanometers thick. Films that are less than 50 nanometers thick, for instance, films that have a thickness between about 1 and about 20 nanometers, also may be produced. Atomic layer deposition films can also be deposited to a desired thickness. For example, films formed can be less than 500 nanometers thick, preferably less than 50 nanometers and more preferably between 2 to 5 nanometers thick.

Organometallic compound precursors described above also can be employed in the method of the invention to form films by atomic layer deposition (ALD) or atomic layer nucleation (ALN) techniques, during which a substrate is exposed to alternate pulses of precursor, reactant gas and inert gas streams. Sequential layer deposition techniques are described, for example, in U.S. Pat. No. 6,287,965 and in U.S. Pat. No. 6,342,277. The disclosures of both patents are incorporated herein by reference in their entirety.

For example, in one ALD cycle, a substrate is exposed, in step-wise manner, to: a) an inert gas; b) inert gas carrying precursor vapor; c) inert gas; and d) a reactant, alone or together with inert gas. In general, each step can be as short as the equipment will permit (e.g. milliseconds) and as long as the process requires (e.g. several seconds or minutes). The duration of one cycle can be as short as milliseconds and as long as minutes. The cycle is repeated over a period that can range from a few minutes to hours. Film produced can be a few nanometers thin or thicker, e.g., 1 millimeter (mm).

The method of the invention also can be conducted using supercritical fluids. Examples of film deposition methods that use supercritical fluid that are currently known in the art include chemical fluid deposition; supercritical fluid transport-chemical deposition; supercritical fluid chemical deposition; and supercritical immersion deposition.

Chemical fluid deposition processes, for example, are well suited for producing high purity films and for covering complex surfaces and filling of high-aspect-ratio features. Chemical fluid deposition is described, for instance, in U.S. Pat. No. 5,789,027. The use of supercritical fluids to form films also is described in U.S. Pat. No. 6,541,278 B2. The disclosures of these two patents are incorporated herein by reference in their entirety.

In an embodiment of the invention, a heated patterned substrate is exposed to one or more organometallic compound precursors, in the presence of a solvent, such as a near critical or supercritical fluid, e.g., near critical or supercritical $CO_2$. In the case of $CO_2$, the solvent fluid is provided at a pressure above about 1000 psig and a temperature of at least about 30° C.

The precursor is decomposed to form a metal film on the substrate. The reaction also generates organic material from the precursor. The organic material is solubilized by the solvent fluid and easily removed away from the substrate. Metal oxide films also can be formed, for example by using an oxidizing gas.

In an example, the deposition process is conducted in a reaction chamber that houses one or more substrates. The substrates are heated to the desired temperature by heating the entire chamber, for instance, by means of a furnace. Vapor of the organometallic compound can be produced, for example, by applying a vacuum to the chamber. For low boiling compounds, the chamber can be hot enough to cause vaporization of the compound. As the vapor contacts the heated substrate surface, it decomposes and forms a metal or metal oxide film. As described above, an organometallic compound precursor can be used alone or in combination with one or more components, such as, for example, other organometallic precursors, inert carrier gases or reactive gases.

In a system that can be used in producing films by the method of the invention, raw materials can be directed to a gas-blending manifold to produce process gas that is supplied to a deposition reactor, where film growth is conducted. Raw materials include, but are not limited to, carrier gases, reactive gases, purge gases, precursor, etch/clean gases, and others. Precise control of the process gas composition is accomplished using mass-flow controllers, valves, pressure transducers, and other means, as known in the art. An exhaust manifold can convey gas exiting the deposition reactor, as well as a bypass stream, to a vacuum pump. An abatement system, downstream of the vacuum pump, can be used to remove any hazardous materials from the exhaust gas. The deposition system can be equipped with in-situ analysis system, including a residual gas analyzer, which permits measurement of the process gas composition. A control and data acquisition system can monitor the various process parameters (e.g., temperature, pressure, flow rate, etc.).

The organometallic compound precursors described above can be employed to produce films that include a single metal or a film that includes a single metal oxide. Mixed films also can be deposited, for instance mixed metal oxide films. Such films are produced, for example, by employing several organometallic precursors. Metal films also can be formed, for example, by using no carrier gas, vapor or other sources of oxygen.

Films formed by the methods described herein can be characterized by techniques known in the art, for instance, by X-ray diffraction, Auger spectroscopy, X-ray photoelectron emission spectroscopy, atomic force microscopy, scanning electron microscopy, and other techniques known in the art. Resistivity and thermal stability of the films also can be measured, by methods known in the art.

Various modifications and variations of this invention will be obvious to a worker skilled in the art and it is to be understood that such modifications and variations are to be included within the purview of this application and the spirit and scope of the claims.

EXAMPLE 1

Synthesis of lithium (N,N'-diisopropylacetamidinate)

A dry 500 milliliter 3-neck round-bottom flask was equipped with a 100 milliliter dropping funnel, a Teflon stir bar, and a thermocouple. The system was connected to an inert atmosphere ($N_2$) nitrogen manifold and the remaining outlets were sealed with rubber septa. To this flask was added 155 milliliters of tetrahydrofuran (THF) and 13.99 grams of diisopropylcarbodiimide. The solution was cooled to –50° C. by use of a dry ice/acetone bath. 72 milliliters of 1.6M MeLi in diethyl ether was added to the dropping funnel. The MeLi solution was added dropwise to the diisopropylcarbodiimide solution at a rate sufficiently slow to keep the temperature of the solution below –30° C. Following the addition the solution was allowed to warm to room temperature overnight. The pale yellow solution can be used either as a solution of lithium N,N'-diisopropylacetamidinate) or the solvent can be removed to isolate the salt.

Synthesis of Bis[dichloro($\eta^6$-benzene)ruthenium (II)]

A procedure adapted from the one outlined in Inorganic Syntheses, Vol 21, page 75 was followed. A dry 500 milliliter 3-neck round-bottom flask was charged with 6 grams of $RuCl_3 \cdot H_2O$ and 300 milliliters of ethanol. The solution was purged with nitrogen. To this solution, 30 milliliters of 1,3-cyclohexadiene was added. The solution was refluxed for 4 hours. Dark orange solids became evident during this time and the color of the solution changed from an opaque, deep orange color to a clear pale yellow solution. The product was filtered through a coarse frit and isolated. 5.8 grams of bis[dichloro($\eta^6$-benzene)ruthenium (II)] was isolated in this manner. The product was dried in a vacuum oven to remove residual ethanol.

Synthesis of Tris(N,N'-diisopropylacetamidinato)ruthenium (III) and Bis(N,N'-diisopropylacetamidinato)dinitrogenruthenium (II)

In a 250 milliliter round-bottomed flask, 5.0 grams of bis[dichloro($\eta^6$-benzene)ruthenium (II)] and a Teflon stir bar were added. The flask was fitted with a thermocouple and reflux condenser and connected to an inert atmosphere/nitrogen manifold, and the remaining outlets were sealed with rubber septa. The flask was evacuated and refilled with nitrogen three times. To this system, 4 equivalents of lithium (N,N'-diisopropylacetamidinate) salt were added as a THF/diethyl ether solution. The solution was refluxed for 16 hours. Following the refluxing of the solution, the solution was filtered, and the solvent was removed under reduced pressure. 3.1 grams of crude material was recovered in this manner. The crude material was sublimed in 2 fractions. The first fraction was initially colorless and developed a pale blue color as the temperature was ramped from 30° C. to 70° C. The second fraction was collected as the temperature of the oil bath beneath the sublimator ramped between 80° C. and 130° C. 120 milligrams of blue crystals were collected.

GC/MS analysis showed two peaks in a cyclohexane solution run of the blue crystals. The first peak integrating for approximately 5% of the total intensity of the two peaks had a mass of 440 Da/e⁻ and showed an isotope pattern consistent with bis(N,N'-diisopropylacetamidinato)dinitrogenruthenium (II) (iPr-Me-AMD)$_2$(N$_2$)$_2$Ru and a fragmentation pattern consistent with the loss of two dinitrogen ligands. The second peak had a mass of 525 Da/e⁻ and showed an isotope pattern and fragmentation pattern consistent with the assignment tris(N,N'-diisopropylacetamidinato)ruthenium (III) (iPr-Me-AMD)$_3$Ru. The reaction scheme can be depicted as follows:

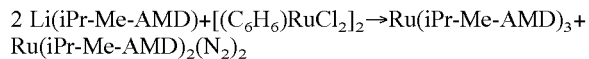

The invention claimed is:

1. A process for the production of an organometallic compound represented by the formula (L)$_2$M(L')$_2$ which process consists essentially of (i) reacting a substituted or unsubstituted metal source compound represented by the formula MX$_2$R with a substituted or unsubstituted amidinate or amidinate-like compound represented by the formula A$_1$L and a ligand source represented by the formula L', said ligand source L' present in an amount sufficient to coordinate directly to M, in the presence of a solvent and under reaction conditions sufficient to produce a reaction mixture comprising said organometallic compound, and (ii) separating said organometallic compound from said reaction mixture;
wherein M is a Group VIII metal, X is a halogen group, R is a substituted or unsubstituted hydrocarbon group, A$_1$ is an alkali metal, L is the same or different and represents a substituted or unsubstituted amidinato group or a substituted or unsubstituted amidinato-like group, and L' is the same or different and represents N$_2$ or a substituted or unsubstituted heteroatom-containing group.

2. The process of claim 1 wherein, in the metal source compound represented by the formula MX$_2$R, M is Ru, Os or Fe, X is fluoro, chloro, bromo or iodo, and R is $\eta^6$-benzene or $\eta^6$-toluene.

3. The process of claim 1 wherein the metal source compound is selected from bis[dichloro($\eta^6$-benzene)ruthenium (II)] and bis[dichloro($\eta^6$-toluene)ruthenium (II)].

4. The process of claim 1 wherein, in the amidinate or amidinate-like compound represented by the formula A$_1$L, A$_1$ is lithium, sodium or bromium and L is an amidinato group or a negatively charged, chelating, four electron donor group.

5. The process of claim 1 wherein the amidinate or amidinate-like compound is selected from lithium (N,N'-diisopropylacetamidinate), lithium (N,N'-diisopropylformamidinate), lithium (N,N'-di-n-propylacetamidinate), lithium (N,N'-di-n-propylformamidinate), lithium (N,N'-diethylacetamidinate), lithium (N,N'-diethylformamidinate), lithium (N,N'-dimethylacetamidinate), and lithium (N,N'-dimethylformamidinate).

6. The process of claim 1 wherein the ligand source represented by the formula L' is selected from N$_2$, NCR$_7$, PR$_7$R$_8$R$_9$ or NR$_7$R$_8$R$_9$, wherein R$_7$, R$_8$ and R$_9$ are the same or different and each represents hydrogen, a halogen atom, an acyl group having from 1 to about 12 carbon atoms, an alkoxy group having from 1 to about 12 carbon atoms, an alkoxycarbonyl group having from 1 to about 12 carbon atoms, an alkyl group having from 1 to about 12 carbon atoms, an amine group having from 1 to about 12 carbon atoms or a silyl group having from 0 to about 12 carbon atoms.

7. The process of claim 1 wherein the organometallic compound comprises bis(N,N'-diisopropylacetamidinato)dinitrogenruthenium (II), bis(N,N'-diisopropylacetamidinato)di-trimethylphosphineruthenium (II), bis(N,N'-diisopropylformamidinato)dinitrogenruthenium (II), bis(N,N'-diisopropylformamidinato)di-trimethylphosphineruthenium (II), bis(N,N'-di-n-propylacetamidinato)dinitrogenruthenium (II), bis(N,N'-di-n-propylacetamidinato)di-trimethylphosphineruthenium (II), bis(N,N'-di-n-propylformamidinato)dinitrogenruthenium (II), bis(N,N'-di-n-propylformamidinato)di-trimethylphosphineruthenium (II), bis(N,N'-diethylacetamidinato)dinitrogenruthenium (II), bis(N,N'-diethylacetamidinato)di-trimethylphosphineruthenium (II), bis(N,N'-diethylformamidinato)dinitrogenruthenium (II), bis(N,N'-diethylformamidinato)di-trimethylphosphineruthenium (II), bis(N,N'-dimethylacetamidinato)dinitrogenruthenium (II), bis(N,N'-dimethylacetamidinato)di-trimethylphosphineruthenium (II), bis(N,N'-dimethylformamidinato)dinitrogenruthenium (II), and bis(N,N'-dimethylformamidinato)di-trimethylphosphineruthenium (II).

8. The process of claim 1 wherein the solvent is selected from saturated and unsaturated hydrocarbons, aromatic hydrocarbons, aromatic heterocycles, alkyl halides, silylated hydrocarbons, ethers, polyethers, thioethers, esters, thioesters, lactones, amides, amines, polyamines, nitriles, silicone oils, other aprotic solvents, or mixtures of one or more of the above.

9. The process of claim 1 wherein the organometallic compound is represented by the formula

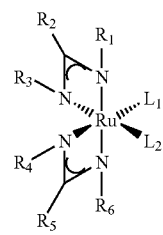

wherein R$_1$, R$_2$, R$_3$, R$_4$, R$_5$ and R$_6$ are the same or different and each represents hydrogen, a halogen atom, an acyl group having from 1 to about 12 carbon atoms, an alkoxy group having from 1 to about 12 carbon atoms, an alkoxycarbonyl group having from 1 to about 12 carbon atoms, an alkyl group having from 1 to about 12 carbon atoms, an amine group having from 1 to about 12 carbon atoms or a silyl group having from 0 to about 12 carbon atoms, and $L_1$ and $L_2$ are the same or different and each represents $N_2$ or a substituted or unsubstituted heteroatom-containing group.

* * * * *